United States Patent [19] [11] 4,384,206
Bjarno [45] May 17, 1983

[54] PROCESS FOR DETECTION OF PARTICULAR QUALITY PROPERTIES IN INDIVIDUAL ARTICLES OF FOOD

[75] Inventor: Ole-Christian Bjarnø, Holte, Denmark

[73] Assignee: Slagteriernes Forskningsinstitut, Roskilde, Denmark

[21] Appl. No.: 232,038

[22] PCT Filed: May 16, 1980

[86] PCT No.: PCT/DK80/00028
§ 371 Date: Jan. 13, 1981
§ 102(e) Date: Jan. 13, 1981

[87] PCT Pub. No.: WO80/02597
PCT Pub. Date: Nov. 27, 1980

[30] Foreign Application Priority Data

May 16, 1979 [DK] Denmark ............................ 2029/79

[51] Int. Cl.$^3$ ...................... G01N 33/12; G01N 21/25
[52] U.S. Cl. .................................... 250/339; 250/341; 436/21; 436/128; 436/96; 436/131; 436/129; 426/231
[58] Field of Search ............ 23/230 R, 230 B, 230 M; 426/248, 232, 641, 332, 231; 250/338, 339, 340, 341; 436/21, 96, 128, 129, 131

[56] References Cited

U.S. PATENT DOCUMENTS 4,009,390 2/1977 Satterlee et al. .................. 23/230 B
4,102,646 7/1978 Sleeter .............................. 23/230 R

OTHER PUBLICATIONS

Chemical Abstracts, vol. 79, 77338e (1973).
Chemical Abstracts, vol. 85, 1580232 (1976).
Welcher, Frank J., *Standard Methods of Chemical Analysis*, Part B, D. Von Nostrand, Inc., New York, pp. 1447, 1450 (1963).

*Primary Examiner*—Michael S. Marcus
*Attorney, Agent, or Firm*—Hubbell, Cohen, Stiefel & Gross

[57] ABSTRACT

Boar taint in individual carcasses of uncastrated boars or parts thereof is determined in a fast and simple manner by determining IR-spectrophotometrical transmission data for the individual carcass or part or preferably on a sample from the carcass or part, and comparing the spectral data registered with corresponding data having a statistical relationship to boar taint. A suitable determination is determination of the ratio between the absorptions at two different wave lengths in the range of 1275–1325 cm$^{-1}$ in the IR spectrum of the fat sample. A still higher correlation between the particular spectral data and the organoleptic data is obtained when one or more further parameters with statistical correlation to the odor image is/are included, e.g., the concentration of unsaturated fatty acids in the fat of the boar carcass.

5 Claims, No Drawings

PROCESS FOR DETECTION OF PARTICULAR QUALITY PROPERTIES IN INDIVIDUAL ARTICLES OF FOOD

The present invention relates to a process for detection of particular quality properties in individual articles of food or raw articles for foodstuffs, i.e. "boar odour and boar taste" ("boar taint") in carcases of non-castrated boars or parts of such carcases, which detection may be incorporated as a natural stage in the production process of treating the carcases with a view to achieving a sufficiently reliable criterion for assessing in which category of two or more organoleptic quality categories the individual carcase or part is to be sorted.

Boar odour and boar taste, called "boar taint" below, are, such as the name suggests, a characteristic of boars which in contradistinction to their sisters (sows) and castrated brothers (hogs) have a characteristic sweat-like or urine-like smell in the meat. As a certain part of the consumers are sensitive towards this smell, all small boars are castrated in Denmark and in most other countries. However, this procedure involves a considerable loss in production as growth and meat quality are considerably lower for castrates than for boars.

However, the point is that only about 5 percent of the boars of normal slaughter weight smell so heavily that it will be inconvenient, and for the reasons stated below it would be desirable if castration could be avoided and those animals which show considerable boar taint could instead be sorted out and used for products in which the taint is concealed.

Until now there has, however, not been any method available through which carcases showing boar taint could be sorted out in a slaughtering line in a sufficiently efficient way.

There are methods for the detection of what is believed to be the main component of the boar taint, i.e. androstenone, but those methods which until now have been tried cannot be considered for an on-line detection in slaughterhouses. The known methods are high pressure liquid chromatography, gas chromatography-mass spectrometry, radioimmunoassay, enzyme-coupled immunosorbent assay and gas-liquid chromatography. All of these methods are complicated, labour-intensive and slow, and they require apparatus which can hardly be used in slaughterhouse environment in continuous operation.

To give an understanding of the problems in connection with the present example of an organoleptic property, that is, boar taint, boar taint will be discussed in greater detail below:

Boar taint was investigated for the first time by Lerche in 1936 (Geschlechtsgeruch bei Eberkastraten, Z. Fleish- u. Milchhyg. 46, 417, (1936)). Thereafter, there were only scarce activities in the field until 1968, when the appearance of the mass spectrometer enabled R. L. S. Patterson (5α-Androst-16-ene-3-one Compound Responsible for Taint in Boar Fat, J.Sci.Fd.Agric., 19, 31–38, (1968)) to identify what he believed was the main component in boar taint and which is still considered the main component in boar taint, i.e. androstenone (5α-androst-16-ene-3-one). In a later article (Identification of 3α-Hydroxy-5α-androst-16-ene as the Mush Odour Compound of Boar Submaxilliary Salivary Gland and its Relationship to the Sex Odour Taint in Pork Meat. J.Sci.Fd.Agric., 19, 434–438, (1968)), Patterson describes the identification of the related compound 3α-hydroxy-5α-androst-16-ene from boar salivary glands and presents the hypothesis that this is the primary olfactory communication compound (sex pheromon) and that surplus thereof is stored in the fat tissue in oxidised form as androstenone. The deposit varies considerably; thus, Øystein Andresen (Øystein Andresen & Håvard Bakke, 5α-Androstenone in Fat from Boars Selected for Rate of Gain and Thickness of Back Fat and from Boars Used in Artificial Insemination Service, Acta. Vet. Scand., 16, 492, (1975)) has found a variation from 0.8 to 7 $\mu g/g$ from the shoulder region to the loin region.

The fact that androstenone is considered to be the main component in boar taint is related to the fact that this compound has a smell which resembles boar taint to a high degree, and that, until now, this is the compound which has been found to have the highest (although not very high) correlation to organoleptic assessments.

That other facts than the androstenone concentration are related to the boar taint appears, for example, from the fact that odour panel investigations on pure androstenone (N. M. Griffith & R. L. S. Patterson, Human Olfactory Response to 5α-Androst-16-ene-3-one as Principal Component of Boar Taint, J.Sci.Fd.Agric., 21, 4–6, (1970)) do not give the same result as on on boar meat. Also, several works have been described which show that other circumstances contribute to the odour image. Thus, J. Wismer-Pedersen (Produktion og smag af ornekød, Konserves & Dybfrost, 4, 38, (1969), and Landøkonomisk Forsøgslaboratorium, Efterårsmøde, p136, (1968)) has demonstrated a positive correlation to the fatty acid composition (the degree of unsaturation) and to the hexanal concentration. The influence of the fatty acid composition has also been investigated in Lund (B. Malmfors, K. Lundström, I. Hansson, Interrelations between 5α-Androstenone, Boar Taint, and Fatty Acid Composition, In. Prep. Dept. of Animal Breeding, Agr. Coll. Uppsala). Vold (E. Vold. Fleischproduktionseigenschaften bei Ebern und Kastraten, Meldinger fra Norges Landbrukshöjskole, No. 16, 49, (1970)) has identified a further component which manifests itself in the boar taint odour immage, that is, skatol, 3-methylindol. Finally, the above-mentioned sex pheromon, androstenol, also occurs in the fat tissue (K. W. Berry & J. D. Sink, Isolation and Identification of 3α-hydroxy-5α-androst-16-ene and 5α-androst-16-ene-3-one from Porcine Adipose Tissue, J. Endocr., 51, 223–224, (1971)), and although it has a pleasant musk-like odour, it must also contribute to the total odour image (R. H. Thompson, A. M. Pearson, K. A. Banks, Identification of some $C_{19}$-$\Delta^{10}$ Steroids, J. Arg. Food Chem., 20, p185, (1972)). Furthermore, a great number of related hormones from boar testicles have been identified (O. B. Gower, 16-Unsaturated $C_{19}$ Steroids. A Review of their Chemistry, Biochemistry, and Possible Physiological Role, J. Steroid Biochemistry, 3, 45, (1972)); in addition to androstenone and androstenol, these are androstenan, androstenandiene, androstadienine, and others, and it is likely that some of these or conversion products thereof also appear in the fat and contribute to the taint.

The hypothesis that it is not only one compound which is responsible for the boar taint is also confirmed by the fact that up till now, many organoleptic investigations have been made, and that the correlation to androstenone has on the whole been about 0.5.

Thus, in three investigations, B. Malmfors (B. Malmfors & Ø. Andresen, Relationship between Boar Taint Intensity and Concentration of 5α-Androst-16-ene- 3-one in Boar Peripheral Plasma and Back Fat, Acta Agr. Scand., 25, 93–95, (1975) and B. Malmfors, K. Lundström, I. Hansson, Interrelations between 5α-Androstenone, Boar Taint, and Fatty Acid Composition, In. Prep. Dept. of Animal Breeding, Agr. Coll. Uppsala) in three investigations finds correlations of about 0.5 with large groups of Swedish Landrace, Yorkshire and hybrids between Swedish Landrace, Yorkshire and Hampshire. From Canada, Newell et al. (J. A. Newell et al., Influence of late Castration and Diethylstilbestrol Implantation on Performance of Boars and on Incidence of Boar Taint, Can. J. Anim. Sci., 53, 205, (1973)) report about a correlation of 0.53. Desmoulin (B. Desmoulin, Recherches sur l'Evelage des Porcs, INRA-CNRZ, 78350 Jony-en-Josas, France, results presented at the 2nd meeting in EAPP Working Group on "Production and Utilization of Meat from Entire Male Animals, 18–19 Oct., 1977") finds correlations of 0.24–0.66 for the races Belgian Landrace and Pitain. At the Slagteriernes Forskningsinstitut (The Danish Meat Research Institute) (Lis Buchter, Sammenhaeng mellem ornelugt og indhold af 5α-androstenon i spaek, Slagteriernes Forsningsinstitut rapport 17/43, (1977)), 0.6 is found for Danish Landrace. The highest correlation ever disclosed is 0.75 (Georg Fuchs, The Correlation Between 5α-Androst-16-ene-3-one Content and the Sex Odour Intensity in Boar Fat, Swedish J. Agric. Res., 1, 233–237, (1971)), but this was from a rather limited number of animals, that is, 20, from which the results of the three highest were left out as it was believed that these could not be distinguished organoleptically.

These correlations or, rather, lack of correlations, may be attributed to three facts: The uncertainty of the organoleptic reference method, the uncertainty of the androstenone determination, and the fact that androstenone alone is not a particularly good indicator for the phenomenon. It is probably most likely that what manifests itself is a combination of all three influences.

The economic advantages in the meat production from boars has always been so evident that many speculations have been made as to how the boar taint could be avoided. It has been attempted to perform castration at a later time when the main part of the meat growth has taken place, or to administer diethylstilbestrol which stops the hormone production, that is, "chemical castration" (J. A. Newell et al., Influence of Late Castration and Diethylstilbestrol Implantation on Performance of Boars and on Incidence of Boar Taint, Can. J. Anim. Sci., 53, 205, (1973)). The average reduction of the odour intensity took place with a factor of 2, but as castration of grown-up pigs is a rather comprehensive operation with considerable risk of complications, and as, anyway, it is only partly effective, this is hardly an attractive solution.

It has also been presumed that there might be differences between the races with respect to their tendency to show boar taint. As a support for this presumption has been mentioned i.a. the fact that English consumers apparently react in a considerably less negative manner to boar meat than continental consumers (A. Landon, Meat from Boars, Pig Farming, July 1977). Birgitta Malmfors (B. Malmfors & I. Hansson, Incidence of Boar Taint in Swedish Landrace and Yorkshire Boars, Livest. Prod. Sci., 1, 411, (1974)) has tried to investigate this and it has been found that the English race Yorkshire has slightly less boar taint than Swedish Landrace. The difference is only just statistically significant and can hardly explain the alleged acceptance of boar meat by the English consumers.

Another aspect which has been investigated is the possibility to subdue the sex odour by selective breeding. This has been investigated by Wismer-Pedersen and P. Jonsson (P. Jonsson & J. Wismer-Pedersen, Kønslugt hos orner af Dansk Landrace, Statens Husdyrbrugsforsøg, Meddelelse nr. 110, 1976), but the material was not statistically reliable. However, a slight positive correlation between six odour and covering willingness was found, and this indicates that if it is attempted to remove, through breeding, a parameter like sex odour which is closely related to central hormonal processes, there is a risk that, at the same time, other (desired) properties such as covering willingness and the like will be disturbed.

Even if it were possible to subdue the sex odour through selective breeding, this would, however, take a long time, i.a. due to the badly estimated selection parameter, and as stated above, it is uncertain whether other (desired) properties can be maintained intact.

In the same manner as the chemical background has not been fully solved, the consumer response on boar meat showing boar taint is also highly varied. The above-mentioned investigations from England indicate that in England, it is by and large possible to market boar meat showing boar taint without reaction from the consumers. Other comprehensive investigations from Holland (P. Walstra, Fattening of Young Boars: Quantification of Negative and Positive Aspects, Livestock Production, Science, 1, 187–196, (1974)) arrive at a similar conclusion, i.e. that consumers generally hardly notice boar taint, but that, in spite of this, boars which show a strong boar taint should anyway be sorted out in consideration of the few especially sensitive persons. Other investigations, for example a recent investigation at the Slagteriernes Forskningsinstitut (Lis Buchter & Asta Vimmerslev, Afprøvning af ornelugtens indflydelse på kvaliteten af svinekødsprodukter, Slagteriernes Forskningsinstitut, rapport 17/43-1 (1977)) showed that consumers clearly gave an inferior rating to boar meat showing boar taint.

Thus, the reaction on boar taint is highly varied which may possibly be due to the fact that considerable psychological moments enter into the evaluation which is, therefore, difficult to quantificate, but even if it is few out of the consumers who are sensitive to the odour of boar meat, it would, in view of the general reputation of bacon products in general, not be desired to expose the consumers to boar taint.

The economy in the production of boar meat has been investigated in great detail. Thus, in A. Landon, Meat from Boars, Pig Farming, July 1977, it is mentioned that the growth for boars is 712 g/day versus 662 g/day for castrates, which means an about 10% larger production from boars and, consequently, about 10% lower capital investments. The utilization of the fodder is stated to be about 10% better than for castrates, and the carcases have 9–20% less fat layer than for castrates, which results in a higher classification. The production loss in castration of male pigs is judged to be about Dkr. 50 per pig, which means that in Denmark, with a production of 5 million hogs, there is a total production loss of 250 million Dkr./year. A similar amount is found by Walstra (P. Walstra, Fattening of Young Boars: Quantification of Negative and Positive Aspects, Livestock Production Science, 1, 187–196, (1974)) for Dutch conditions, and for the EEC in total, the production loss has been estimated at 3 billion Dkr./year.

Therefore, there is a great demand for an automatable standard analysis method for the detection of boar taint which enables fast and sufficiently reliable sorting out of carcases showing boar taint in the production line at a slaughter house, as the procurement and utilisation of such automatable standard analysis method would make it possible, without any risk to the reputation of the bacon production, to abstain from castration of male pigs and thereby to enjoy the very great economical advantages connected therewith. However, the existing methods for detecting boar taint are not suitable for this purpose:

Today, two categories of methods are used for detecting boar taint, that is, direct methods (organoleptic methods) and indirect methods (chromatographical, immunological and mass-spectrometrical methods).

The traditional organoleptic method may, e.g., be performed by placing a slice of bacon on a glass Petri dish in an oven at 200° C. for 6–7 minutes, whereafter the slice is rated by an experienced taste panel of 8 persons.

In recent years, some experimentation has been made with a variant of this method, that is, the so-called handsealer or soldering bolt. This consists of a soldering bolt with a specially designed point which is thermostated to 150° C., and the method comprises first placing the bolt on the fat for some seconds and thereafter placing the bolt under one's nose. The handsealer method is faster than the traditional method, although hardly quite as reliable, and has spread widely and is even alleged to be useful for separation of boars showing boar taint on the slaughtering line (P. Walstra, G. Maleman, P. C. Moerman, Het Gebruick van De Handsealer in De Slachtlijn Ter Vaststilling van Beregeur, Tijdschr. Diergeneesk. dul/02, afl. 15, p. 913 (1977)), but the exactitude must be presumed to be too low.

The organoleptic reference method is clearly subject to a considerable variation, but when performed correctly using large taste panels, with consideration to psychology, adaptation, individual variation and the like, it constitutes a reasonably good tool. However, the method will hardly be useful for the separation on the slaughtering line as it is too laborious to be economical.

The other known methods all detect androstenone and all require an extraction, fractionation and purification. This separation procedure may be performed in various manners, but as a typical separation procedure may be mentioned (W. D. Hubbard et al., Comparison of Various Methods for the Extraction of Total Lipids, Fatty Acids, Cholesterol, and other Sterols from Food Products, J. of AOCS, 54, p. 81 (1977)): extraction with chloroform/methanol, homogenisation in a blender, filtration washing with water, phase separation, washing of water phase and evaporation of solvent.

Another example (O. Andresen, A Radioimmunoassay for 5α-Androst-16-ene-3-one in Porcine Adipose Tissue, Acta Endocrinologica, 79, 619–624 (1975)) is: fat tissue is homogenised in absolute ethanol and is thereafter centrifuged, the supernatant is separated and cooled down with dry ice/acetone, then centrifugation is again performed and the supernatant is separated, whereafter the solvent is carefully evaporated.

It is evident that sample preparation procedures of this character are not exactly suitable in an automated, fast detection method. Among chromatographic methods, thin layer chromatography (R. Claus, B. Hoffman, H. Karg, Determination of 5α-Androst-16-ene-3-one, a Boar Taint Steroid in Pigs, with Reference to Relationships to Testosteron, J. Anim. Sc., 33, p. 1293 (1971)), gas chromatography (J. Wismer-Pedersen, Landøkonomisk Forsøgslaboratorium, Efterårsmøde, p. 136 (1968)) as well as high pressure liquid chromatography and gas/liquid chromatography (O. B. Gower, 16-Unsaturated $C_{19}$ Steroids. A Review of Their Chemistry, Biochemistry, and Possible Physiological Role, J. Steroid Biochemistry, 3, 45 (1972)) have been used. All these methods have not been given up because of failing sensitivity and have been replaced by radioimmunoassay. All teams of scientists in Europe (about 5) working with determination of androstenone use radioimmunoassay (RIA).

Briefly, radioimmunoassay comprises coupling the androstenone, subsequent to separation and purification, to a radioactively labelled androstenone-antibody. After separation of the antigen/antibody complex, the remaining radioactivity is determined as a measure of the androstenone concentration.

The method is sensitive and reasonably reliable (interlaboratory deviations of up to a factor of 2 have, however, been reported), but it is a pronounced laboratory method which additionally requires isotope laboratory.

Another variant of the immunological method, in which variant the necessity of an isotope laboratory can be avoided, is ELISA, or enzyme-coupled immunosorbent assay. Originally, the method was developed and instrumentated for detection of hepatitis virus in blood banks, but it has also been used, e.g., for the detection of antibodies against trichinae in pigs in slaughterhouses (Ruitenberg et al., Application of ELISA for the Serodiagnosis of T. Spirales Infections in Pigs under Slaughterhouse Conditions, Proc. IIIrd Int. Congress of Parasitology, Müchen, 1203 (1974)) and would be adaptable to androstenone determination in slaughterhouses. However, the method uses various expensive chemicals and does not immediately seem to be especially well suited for use under slaughterhouse conditions, and it requires a complete sample preparation with weighing out of fat tissue, extraction, separation and purification.

The mass spectrometrical methods show the same disadvantages as are mentioned above in connection with chromatographical methods, as the separation step in the mass spectrometrical methods is performed by gas chromatography.

The present invention provides a method for detecting boar taint in individual carcases of uncastrated boars or parts thereof, which method is suitable for on-line utilisation in slaughterhouses or other industries treating the individual boar carcases or parts thereof, and the method is characterised in that IR spectrophotometrical transmission data are determined for the individual carcase or part, and spectral data thus registered are compared with corresponding data having a statistical relationship to boar taint.

The IR spectrophotometrical transmission data having a statistical relationship to boar taint may be found empirically or through a combination of theoretical considerations and empirical experiments, using, for this purpose, well-known statistical methods for assessing the relationship between boar taint and the spectral data contemplated for use as a basis for the correlation determination. These assessments can be performed by the skilled art worker on the basis of the inventive recognition of the fact that IR spectrophotometrical transmission data do exist which have a statistical correlation with boar taint, and that such spectral data may be used in a simple, automatable and convincing manner as a basis for a reliable sorting according to organoleptic criteria.

When IR transmission measurement is performed on a sample from the individual boar carcase or part, this sample may be any sample which as been directly taken from the individual carcase or part or any preparation or derivative of the sample from the individual carcase or part suitable for the determination in question, for example an extract of fat tissue from the individual boar or a vapour phase provided by evaporation of fat from the individual boar carcase.

In contradistinction to the above-mentioned known methods which have been experimentally used for the determination of boar taint in slaughterhouses, IR transmission analyses are advantageous in that they may be performed fast and exactly in suitable apparatus, and when they use samples from the individual boar carcase or part, they may be adapted in such a manner that the sample preparation becomes reasonable for the purpose. A special advantage of suitable determinations for the purpose of the invention is that it is not necessary to perform any weighing out of the sample in cases where a standardised sample preparation technique is combined with transmission measurements in a cuvette with a predetermined light path, or, which is especially suitable, in cases where the statistical correlation to boar taint is related to the ratio between transmission or absorption at two distinct wave lengths in the IR spectrum such as is illustrated in Example 1, as in these cases, the size or weight of the sample is not significant to the results, except that the samples should be of a order of size which is suitable for the determination in question.

The sample withdrawal in the process of the invention may be performed with various levels of automation. For example, at the start of the slaughtery line, a portion of fat tissue may be cut out which, subsequent to coding in the number of the pig, is transported, for example, on a cup elevator/conveyor, to an analysis automate where the further sample preparation consists of heating of the sample to fluid consistency and aspiration of the fluid fat into the measuring cuvette. In this connection, it may be suitable to perform a filtration or centrifugation of the fluid fat. Furthermore, it is suitable that the flow system in the analysis automate is cleaned automatically, for example with detergent/deionized water.

If the sample from the carcase is evaporated, the sample withdrawal may simply be performed by aspiration which may be performed in an almost fully automated manner. Thus, at the classification station, such burning-sample-withdrawal may be performed either by means of a specific probe or a function built together with the conductivity probe already in use.

The further analysis of the combustion gasses should be performed in a very sensitive system, and for this purpose, IR laser systems are attractive. For example, an IR LOS system (Laser Optoacoustic Spectroscopy) may, in a couple of minutes, analyse a mixture of 10 gasses with a sensitivity which, in practice, is about 1 ppb (L. B. Kreutzer., Laser Optoacoustic Spectroscopy. A New Technique of Gas Analysis, Analytical Chemistry, 46, 240A, (1974); and L. B. Kreutzer, N. D. Kenyon, C. K. N. Patel, Air Pollution: Sensitive Detection of Ten Gases by Carbon Monoxide and Carbon Dioxide Lasers, Science, 177, page 347, (1972)) and with a theoretical detection limit of $10^{-3}$ (L. B. Kreutzer, Ultralon Gas Concentration Infrared Absorption Spectroscopy, J. of Applied Physics, 42, 2934, (1971)). Such systems are robust and suitable for industrial process control (L. B. Kreutzer, Laser Optoacoustic Spectroscopy. A New Technique of Gas Analysis, loc. cit.).

According to the invention, a sufficiently reliable determination may be obtained on the basis of a single IR spectral parameter. Thus, the IR absorption in the wave length range of 1275-1335 $cm^{-1}$, especially 1300-1310 $cm^{-1}$, has shown a correlation coefficient of 0.6-0.8 to boar taint with a standard deviation of ½ taint rating according to a series from $-5$ (best taint) to $+5$ (worst taint; the most pronounced boar taint). In Example 1, an especially suitable parameter is exemplified, that is, the relation between absorption at two different wave lengths in the IR spectrum, especially in the same range of 1275-1325 $cm^{-1}$. A still higher correlation between the data determined in the process of the invention and the organoleptic data may be obtained by determining one or more further parameters with statistical correlation to boar taint and using the correlation between the determination of the further parameter or parameters for the individual boar carcase or part and corresponding data having a statistical relationship to boar taint as an additional parameter or additional parameters in a statistical analysis, for example performed by multiple correlation or discriminant analysis in the detection of whether the boar carcase or part shows boar taint. Thus, for example, the concentration of androstenone, hexanal and skatol in the fat of the boar carcase, or especially the concentration of unsaturated fatty acids in the fat of the boar carcase, for example determined as refractive index or iodine number, are parameters having a statistical correlation to the odour image (the higher concentration, the higher likelihood of boar taint), and which advantageously may be incorporated in a statistical analysis, e.g. multiple correlation, to obtain increased correlation coefficients. Example 2 illustrates the increase of the correlation coefficient obtained when an IR determination on the melted fat is combined with the chemical determination of the iodine number as an expression of the degree of unsaturation of the fatty acids present in the fat.

In addition to iodine number determination or refractive index determination, a measure of unsaturation may also suitable be obtained by direct IR transmission measurement, e.g. a measurement at about 3000 $cm^{-1}$, where it has been found that there is a high correlation to the iodine number such as appears from the table below showing iodine number in relation to IR transmission measurement for 5 boar samples (measured with a Perkin-Elmer IR spectrophotometer):

TABLE

| Iodine number g/100 g | IR (transmission at 3004 $cm^{-1}$ divided by transmission at 2992 $cm^{-1}$) |
|---|---|
| 61.4 | 0.709 |
| 63.4 | 0.686 |
| 62.5 | 0.693 |
| 64.1 | 0.680 |
| 59.3 | 0.725 |

The correlation coefficient is 0.99.

This means that a particularly high correlation may be obtained when a measurement in the range of 1275-1325 $cm^{-1}$, either of the absorption at a single wave length in this range or of the ratio between the absorptions at two different wave lengths in this range, is combined with a measurement at about 3000 cm$^{-1}$ which serves to establish a measure of the iodine number in the statistical analysis, for example the multiple correlation with the discriminant analysis. In addition, the statistical analysis may include the result of a measurement at other wave lengths giving an improved correlation to boar taint.

EXAMPLE 1

From each of a series of 10 pieces of streaky bacon from a sow and 9 boars, respectively, fat was extracted in the following manner: 45 g of meat sample were extracted with 50 ml of perchloroethylene for 2 minutes in a Foss-Let reactor (a closed steel container in which the sample together with perchloroethylene is subjected partly to shaking and partly to working with a reciprocating piston), and the extract containing the major part of the fat content of the sample was filtered through kieselguhr and was thereafter ready for the following investigations.

The filtrates from the 10 samples were transferred to the cuvette in a Perkin-Elmer Infrared Spectrophotometer 580, by means of which transmittances were measured in frequencies around the peak at about 1280 cm$^{-1}$ with a referene plateau at about 1300 cm$^{-1}$. Between the measurements, the cuvette was first flushed with perchloroethylene, thereafter twice with the next sample to be measured, and after a third thorough flushing, the measurement was performed.

On samples from each piece, organoleptic determination with a flavour panel of 8 persons was also performed. The results appear from the table below:

TABLE I

Ratio peak wave length/reference wave length for sow meat and boar meat, respectively, at various taint ratings according to a series from 0 (best taint) to 5 (worst taint)

| $\lambda^1/\lambda^2$ | 1300/1280 | 1300/1275 | 1300/1270 | 1295/1280 | 1295/1275 |
|---|---|---|---|---|---|
| Sow | 1.1235 | 1.1463 | 1.1701 | 1.1111 | 1.1359 |
| 0.0 | 1.1247 | 1.1531 | 1.1777 | 1.1189 | 1.1446 |
| 0.38 | 1.1173 | 1.1415 | 1.1643 | 1.1057 | 1.1316 |
| 0.38 | 1.1210 | 1.1484 | 1.1722 | 1.1111 | 1.1359 |
| 0.50 | 1.1208 | 1.1457 | 1.1694 | 1.1129 | 1.1356 |
| 0.75 | 1.1171 | 1.1420 | 1.1656 | 1.1091 | 1.1362 |
| 1.62 | 1.1208 | 1.1460 | 1.1698 | 1.1131 | 1.1379 |
| 2.12 | 1.1171 | 1.1392 | 1.1620 | 1.1075 | 1.1292 |
| 3.38 | 1.1090 | 1.1346 | 1.1569 | 1.1015 | 1.1248 |
| 3.75 | 1.1054 | 1.1259 | 1.1472 | 1.0941 | 1.1167 |
| Correlation co-efficient | 0.90 | 0.88 | 0.88 | 0.81 | 0.85 |
| $\lambda^1/\lambda^2$ | 1295/1270 | 1290/1280 | 1290/1275 | 1290/1270 | 1300/1285 |
| Sow | 1.1618 | 1.0932 | 1.1197 | 1.1408 | 1.0658 |
| 0.0 | 1.1692 | 1.1002 | 1.1282 | 1.1524 | 1.0661 |
| 0.38 | 1.1540 | 1.0863 | 1.1139 | 1.1363 | 1.0639 |
| 0.38 | 1.1615 | 1.0911 | 1.1176 | 1.1408 | 1.0682 |
| 0.50 | 1.1612 | 1.0930 | 1.1174 | 1.1405 | 1.0642 |
| 0.75 | 1.1598 | 1.0934 | 1.1199 | 1.1435 | 1.0644 |
| 1.62 | 1.1615 | 1.0933 | 1.1199 | 1.1408 | 1.0665 |
| 2.12 | 1.1540 | 1.0921 | 1.1135 | 1.1357 | 1.0622 |
| 3.38 | 1.1468 | 1.0846 | 1.1075 | 1.1314 | 1.0571 |
| 3.75 | 1.1399 | 1.0818 | 1.1018 | 1.1248 | 1.0555 |
| Correlation coefficient | 0.87 | 0.72 | 0.84 | 0.82 | 0.88 |
| $\lambda^1/\lambda^2$ | 1305/1280 | 1305/1285 | | 1310/1280 | 1310/1285 |
| Sow | 1.1403 | 1.0866 | | 1.1640 | 1.1071 |
| 0.0 | 1.1502 | 1.0897 | | 1.1728 | 1.1113 |
| 0.38 | 1.1338 | 1.0801 | | 1.1568 | 1.1040 |
| 0.38 | 1.1389 | 1.0870 | | 1.1647 | 1.1075 |

TABLE I-continued

Ratio peak wave length/reference wave length for sow meat and boar meat, respectively, at various taint ratings according to a series from 0 (best taint) to 5 (worst taint)

| 0.50 | 1.1431 | 1.0849 | 1.1647 | 1.1077 |
|---|---|---|---|---|
| 0.75 | 1.1349 | 1.0813 | 1.1567 | 1.1021 |
| 1.62 | 1.1440 | 1.0875 | 1.1680 | 1.1061 |
| 2.12 | 1.1346 | 1.0804 | 1.1555 | 1.1005 |
| 3.38 | 1.1316 | 1.0789 | 1.1498 | 1.0966 |
| 3.75 | 1.1215 | 1.0729 | 1.1415 | 1.0920 |
| Correlation coefficient | 0.74 | 0.77 | 0.80 | 0.90 |

It will be noted that the maximum correlation coefficient is obtained at the ratios 1300/1280 and 1310/1285, but that the other correlation coefficients are also quite satisfactory. When using this system, it will be suitable to sort out carcases having a taint rating of 2 or worse, which will correspond to a ratio between peak wave length absorption and reference wave length absorption of about 1.12.

Thereafter, 7 chop pieces were analysed by determination of the absorption at 1310 and 1285 cm$^{-1}$, respectively, and determination of the ratio between the absorptions. The taint ratings varied evenly from 0.12 to 3.38 when determined according to a series from 0 (best taint) to 5 (worst taint; most pronounced boar taint). The correlation coefficient was found to be 0.88.

EXAMPLE 2

On 10 samples of fat melted from boars, organoleptic taint determination was performed with a flavour panel of 8 persons. The samples were evaluated according to a series with ratings from +5 to −5. The negative part of the series indicates increasingly bad taint. The results appear from the table below in the column "Organoleptic taint rating", as average of the evaluation by the 8 persons.

The fat samples were melted from a minced sample withdrawn from the individual boar carcase. The minced sample was placed in a glass beaker on a sand bath, the temperature of the sand bath being such that the sample temperature was between 50° and 60° C. As soon as a reasonable portion of fat had been melted off, the fat was decanted, and the melted fat was kept in refrigerator in plastic beakers, as it had been found that when standing at room temperature, the samples were subject to changes, presumably by going rancid, and gave other IR results. IR spectrophotometric determinations were performed on fluid fat from the 10 samples. In the table below, the results are stated as the ratio between the transmittance at 1300 cm$^{-1}$ and the transmittance at 1275 cm$^{-1}$.

The apparatus used is a modified "Milko-Scan" 203, which is an IR spectrophotometer especially developed for measurement of fat, protein and lactose in milk, and which is described in detail in "The Analysis of Milk by Infrared Absorption", A Thesis submitted for the Degree of Batchelor of Philosophy at the University of York, by John Shields, November 1975. For the present purpose, the apparatus was modified in the following manner: 4 of the 6 optical filters of the apparatus had been changed in order to measure the wave length ratios at 1300 cm$^{-1}$/1275 cm$^{-1}$ and 1300 cm$^{-1}$/1235 cm$^{-1}$, these ratios being directly read out and simultaneously printed on a connected printer. The cuvette and the interior of the apparatus were thermostated to 50°

C. to ensure that the fat was kept fluid in the cuvette. The otherwise built-in homogeniser of the apparatus, used for milk, had been removed, and the fat was manually injected directly into the cuvette. In comparison with the normal version, the sensitivity of the apparatus had been increased through higher amplification in the electrical circuit, which necessitated measurement on a standard to enable correction for apparatus drift. As a standard, pure commercial lard was used.

In the measurement, the cuvette (cuvette path 37 μm) was first thoroughly flushed with the sample, whereafter three 10-fold determinations were performed on the sample, new sample material being flushed through the cuvette prior to each 10-fold determination. Before and after the sample, 10-fold determination on the standard was performed, and the result for the sample was corrected with the average of the standard measurements.

Column 3 in the following table shows the taint rating obtained when linear correlation between organoleptically determined taint and IR measurement is performed and the taint is read out by means of the resulting correlation equation.

Column 4 of the table states the iodine number, which is a measure of the degree of unsaturation, determined by the chemical standard method. The unit is g of iodine per 100 g of fat. Finally, column 5 states the taint rating obtained when multiple regression analysis is performed between organoleptically determined taint, IR-measured ratio and iodine number.

As will be noted from the table and the calculations of correlation coefficients stated below the table, the use of a multiple correlation results in a considerable increase of the correlation coefficient.

It is possible to use other statistical methods than regression and multiple regression analysis in the treatment of the data material. For example, the data for the 10 samples have been treated in a discriminant analysis. By this, it was possible to sort the samples perfectly into three groups with the limits taint $> -1$, $-1 > $ taint $> -2.5$ and taint $> -2.5$.

TABLE II

| | | Melted fat measured on modified Milko-Scan 203 | | |
|---|---|---|---|---|
| Readout 1300/ 1275 | Organo- leptic taint rating | Taint determined via IR measure- ment (linear regression) | Iodine num- ber g/100 g | Taint determined via IR measure- ment and iodine number (multiple linear regression) |
| 0.27 | 0.25 | −0.75 | 70.95 | −0.72 |
| 0.25 | 0.00 | −1.05 | 70.77 | −1.10 |
| 0.31 | −0.50 | −0.13 | 73.77 | −0.57 |
| 0.22 | −1.00 | −1.51 | 64.78 | −0.28 |
| 0.21 | −1.50 | −1.66 | 67.00 | −1.02 |
| 0.17 | −1.75 | −2.27 | 65.50 | −1.49 |
| 0.17 | −1.88 | −2.27 | 70.30 | −2.64 |
| 0.16 | −2.62 | −2.43 | 70.05 | −2.74 |
| 0.25 | −3.12 | −1.05 | 75.00 | −2.12 |
| 0.14 | −3.50 | −2.73 | 70.20 | −3.24 |

TABLE II-continued

| Melted fat measured on modified Milko-Scan 203 | | | |
|---|---|---|---|
| | | Organoleptic determination versus IR measurement | Organoleptic determination versus IR measurement and iodine number determination |
| Correlation coefficient | R | 0.68 | 0.85 |
| Index of determination | $R^{12}$ | 0.46 | 0.73 |
| Adjusted index of determ. | $R^{12}$ | 0.39 | 0.65 |

$$R^{12} = \frac{N-1}{N-P} \times R^2 - \frac{P-1}{N-P}$$

N = number of measurements
P = number of independent variables

What is claimed is:

1. A method for detecting boar taint in individual carcases of uncastrated boars or parts thereof, comprising determining, by I.R. transmission spectrophotometry, and I.R. spectral parameter of a sample derived from a carcase of uncastrated boars or parts thereof, the I.R. spectral parameter being either (1) the I.R. absorption in the wavelength range of 1275–1335 cm$^{-1}$ or (2) the relation between the I.R. absorption at two different wavelengths in the range of 1275–1325 cm$^{-1}$ in the I.R. spectrum, said spectral parameter having a statistical relationship to boar taint on a fat sample from the individual carcase or part thereof, and thereafter estimating the boar taint from a predetermined relation between the I.R. spectral parameter and the boar taint.

2. The method according to claim 1, wherein the (1) I.R. absorption is in the wavelength range of 1300–1310 cm$^{-1}$.

3. A method according to claim 1, additionally comprising determining an additional parameter with statistical correlation to boar taint, the additional parameter being the concentration of androstenone, hexanal and skatol in the fat of the boar carcase, correlating the additional parameter with corresponding data having a statistical relationship to boar taint, and using the correlation as a further parameter in a statistical analysis for detecting whether the boar carcase or part thereof exhibits boar taint.

4. A method as claimed in claim 3, additionally comprising determining another additional parameter with statistical correlation to boar taint, said another additional parameter being the concentration of unsaturated fatty acids in the fat of the boar carcase, correlating the another additional parameter with corresponding data having a statistical relationship to boar taint, and using said correlation as another further parameter in a statistical analysis for detecting whether the boar carcase or part thereof shows boar taint.

5. A method according to claim 4, wherein the concentration of unsaturated fatty acids in the fat of the boar carcases or parts thereof is determined as refractive index or by I.R. transmission measurement.

* * * * *